United States Patent [19]
Campbell et al.

[11] Patent Number: 5,413,759
[45] Date of Patent: May 9, 1995

[54] PLASMA STERILIZER AND METHOD

[75] Inventors: Bryant A. Campbell, Late of Los Gatos, Calif., by Louise A. Campbell, legal representative; Kern A. Moulton, Livermore, Calif.

[73] Assignee: ABTOX, Inc., Mundelein, Ill.

[21] Appl. No.: 73,653

[22] Filed: Jun. 7, 1993

Related U.S. Application Data

[60] Continuation-in-part of Ser. No. 817,714, Jan. 7, 1992, abandoned, which is a division of Ser. No. 576,292, Aug. 31, 1990, Pat. No. 5,115,166, which is a continuation-in-part of Ser. No. 475,602, Feb. 6, 1990, abandoned, and a continuation-in-part of Ser. No. 321,483, Mar. 8, 1989, abandoned.

[51] Int. Cl.$^6$ ............................................. A61L 2/00
[52] U.S. Cl. .................................... 422/23; 422/22; 422/906
[58] Field of Search ............................. 422/22, 23, 906

[56] References Cited

U.S. PATENT DOCUMENTS

| | | |
|---|---|---|
| 3,383,163 | 5/1968 | Menashi . |
| 3,410,776 | 11/1968 | Bersin . |
| 3,428,548 | 2/1969 | Hollahan . |
| 3,704,096 | 11/1972 | Verses et al. . |
| 3,737,608 | 6/1973 | Nagao et al. . |
| 3,851,436 | 12/1974 | Fraser et al. . |
| 3,948,601 | 4/1976 | Fraser et al. ................ 422/23 |
| 4,065,369 | 12/1977 | Ogawa et al. ............... 204/164 |
| 4,123,663 | 10/1978 | Horiike ........................ 250/531 |
| 4,138,306 | 2/1979 | Niwa ........................... 156/345 |
| 4,151,034 | 4/1979 | Yamamoto . |
| 4,160,690 | 7/1979 | Shibagaki .................... 156/643 |
| 4,169,123 | 9/1979 | Moore et al. ................. 422/29 |
| 4,169,124 | 9/1979 | Forstrom et al. ............. 422/33 |
| 4,207,286 | 6/1980 | Gut Boucher ................. 422/21 |

(List continued on next page.)

FOREIGN PATENT DOCUMENTS

| | | |
|---|---|---|
| 109352 | 5/1983 | European Pat. Off. . |
| 268396 | 5/1989 | German Dem. Rep. . |
| 2214081 | 1/1989 | United Kingdom . |
| 2253144 | 1/1991 | United Kingdom . |

OTHER PUBLICATIONS

Ross Caputo et al., "Alternative Sterilization Technologies Come of Age," *Medical Device and Diagnostic Industry*, V. 14, No. 12, pp. 41–42 (1992).

Leaper et al., "Influence of Temperature on the Synergistic Sporicidal Effect of Peracetic Acid Plus Hydrogen Peroxide on *Bacillus subtilis*" AS22 (NCA 72-52), *Food Microbiology*, 1:199–203, 1984.

(List continued on next page.)

*Primary Examiner*—Robert J. Warden
*Assistant Examiner*—Krisanne M. Thornton
*Attorney, Agent, or Firm*—Majestic, Parsons, Siebert & Hsue

[57] ABSTRACT

A method for plasma sterilization includes exposing an article to be sterilized to a plasma generated from a gas mixture. The gas mixture being either (a) argon, helium, nitrogen, or mixtures thereof, and oxygen and hydrogen; (b) argon, helium, nitrogen or mixtures thereof, and hydrogen; or (c) argon, helium, nitrogen or mixtures thereof, and oxygen. The exposure of the article to the plasma is carried out at a pressure of from 0.1 to 10 torr and a chamber temperature of less than 63° C. for a time period sufficient to effect sterilization. Contaminated articles can be pretreated in a plasma generated from oxygen and optionally argon, helium and/or nitrogen at the same conditions for up to 5 minutes to remove protein. The apparatus for plasma sterilization of articles includes a plasma generator and a sterilizing chamber. The plasma generator includes a plurality of generator tubes positioned in one or more electromagnetic field zones defined by one or more waveguides. The outlet of the generator tube preferably has a restriction for maintaining the gas pressure in the plasma generating chamber at from 0.3 to 10 torr.

8 Claims, 9 Drawing Sheets

U.S. PATENT DOCUMENTS

| | | | |
|---|---|---|---|
| 4,230,663 | 10/1980 | Forstrom et al. | 422/33 |
| 4,289,728 | 9/1981 | Peel et al. | 422/24 |
| 4,321,232 | 3/1982 | Bithell | 422/23 |
| 4,348,357 | 9/1982 | Bithell | 422/22 |
| 4,366,125 | 12/1982 | Kodera et al. | 422/295 |
| 4,437,567 | 3/1984 | Jeng | 206/210 |
| 4,640,782 | 2/1987 | Burleson | 210/748 |
| 4,643,876 | 2/1987 | Jacobs et al. | |
| 4,801,427 | 1/1989 | Jacob | 422/23 |
| 4,818,488 | 4/1989 | Jacob | 422/23 |
| 4,898,715 | 2/1990 | Jacob | |
| 4,917,586 | 4/1990 | Jacob | 422/21 |
| 4,931,261 | 6/1990 | Jacob | 422/292 |
| 4,943,417 | 6/1990 | Jacob | |
| 4,976,920 | 12/1990 | Jacob | |

OTHER PUBLICATIONS

Leaper et al., "A Note on the Effect of Storage on the Chemical Resistance of Spores of *Bacillus subtilis* SA22 and *Bacillus subtilis* Glogigii B17," *J. Applied Biology* 64:183–186, 1988.

Leaper et al., "Synergistic Killing of Spores of *Bacillus subtilis* by Peracetic Acid and Alcohol," *J. Food Technology*, 19:355–360, 1984.

Ross A. Caputo et al., "Validation Testing of a Gas Plasma Sterilization System", *Medical Device and Diagnostic Industry*, vol. 15, #1, pp. 132–138, 1993.

Leaper et al., "Comparison of the Resistance to Hydrogen Peroxide of Wet and Dry Spores of *Bacillus subtilis* SA222," J. Food Technology, 19:695–702, 1984.

Ross A. Caputo et al., "AbTox Plazlyte TM plasma sterilization", Cold Sterilization Beyond 1995: A Look At Alternatives To 12/88 EtO, *Journal of Healthcare Material Management*, vol. 10, No. 8, Sep., 1992.

A. Russell (Ed.), *The Destruction of Bacterial Spores*, New York: Academic Press (1982).

Fraser et al., "Plasma Sterilization Technology for Spacecraft Applications", NASA-CR-146314 Final Report (Boeing Co.), Sep. 1975.

Hallohan et al., "Analytical Applications of Electrodelessly Discharged Gases" Chemical Instrumental, Journal of Chem. Education, 43:A401–A416.

Hallohan et al., "Research with Electrodelessly Discharged Gases," Chemical Instrument, 43:A497–A512.

Hallohan et al., "Chem. Education Letters", Journal of Chem. Education 43:392–393.

Hallohan et al., "Techniques and Applications of Plasma Chemistry," v–v11, 229–253.

Rudder et al., "Remote Plasma-Enhanced Chemical-Vapor Deposition of Epitaxial Ge Films," J. Appl. Phys., 60(1):3522.

PLASMA STERILIZER AND METHOD

This is a continuation-in-part of application Ser. No. 07/817,714, filed Jan. 7, 1992, now abandoned which is a division of application Ser. No. 576,292, filed Aug. 31, 1990, now U.S. No. 5,115,166 which was a CIP of applications Ser. No. 07/321,483 filed Mar. 8, 1989, now abandoned and Ser. No. 07/475,602 filed Feb. 6, 1990, now abandoned.

FIELD OF THE INVENTION

This invention relates to sterilization of articles with gaseous plasmas. In particular this invention relates to an apparatus and method for sterilizing articles with a gas plasma generated from a mixture of oxygen; argon, helium and/or nitrogen; and hydrogen gases.

BACKGROUND OF THE INVENTION

A variety of gas sterilization methods has been investigated in the past. Methods using ethylene oxide and other disinfecting gases are widely used for sterilizing a wide range of medical products from pharmaceutical preparations to surgical instruments. Irradiation alone or together with disinfecting gases has also been investigated, as summarized by Russell, A. THE DESTRUCTION OF BACTERIAL SPORES. New York: Academic Press (1982).

A sterilizing method must effectively kill all organisms, including spores, without damage to the article or goods being sterilized. However, many disinfecting gases which meet this criteria, such as ethylene oxide and irradiation methods, have been recognized to expose workers and the environment to safety hazards. States and Federal legislation are severely restricting the amount of hazardous gases such as ethylene oxide (a carcinogen) in the working environment, or the use of any system or method which produces toxic residues or exhaust products. This is presenting a major crisis in hospitals and other areas of the health industry.

DESCRIPTION OF THE PRIOR ART

The use of plasma to sterilize containers was suggested in U.S. Pat. No. 3,383,163. Plasma is an ionized body of gas which may be generated by the application of power from different sources. The ionized gas will contact microorganisms on the surfaces of the items to be sterilized and effectively destroy the microorganisms.

Sterilizing plasmas have been generated with a wide variety of gases: argon, helium or xenon (U.S. Pat. No. 3,851,436); argon, nitrogen, oxygen, helium or xenon (U.S. Pat. No. 3,948,601); glutaraldehyde (U.S. Pat. No. 4,207,286); oxygen (U.S. Pat. No. 4,321,232); oxygen, nitrogen, helium, argon or freon with pulsed pressure (U.S. Pat. No. 4,348,357); hydrogen peroxide (U.S. Pat. No. 4,643,876); nitrous oxide, alone or mixed with oxygen, helium or argon (Japanese Application Disclosure No. 103460-1983); and nitrous oxide, alone or mixed with ozone (Japanese Application No. 162276-1983). Unfortunately, these plasmas have proven to be too corrosive to articles being sterilized, and particular packaging materials; have left toxic residues on the sterilized articles; or have presented safety or environmental hazards.

Non-plasma gas sterilization procedures have been described using ozone (U.S. Pat. No. 3,704,096) and hydrogen peroxide (U.S. Pat. Nos. 4,169,123, 4,169,124, 4,230,663, 4,366,125, 4,289,728, 4,437,567 and 4,643,876). These materials are toxic and leave undesirable residues.

Plasma gas sterilizer systems described in U.S. Pat. Nos. 3,851,436 and 3,948,601 comprise a plasma RF generation chamber. A gas plasma produced in the chamber with argon, helium, nitrogen, oxygen or xenon is passed into a separate sterilization vacuum chamber. U.S. Pat. No. 4,643,876 describes a hydrogen peroxide plasma RF generation chamber which also functions as the sterilizing chamber. Matching networks are required with the RF systems to adjust to the conductivity variations in the plasma generating zone.

OBJECTS AND SUMMARY OF THE INVENTION

It is an object of this invention to provide a plasma sterilizing apparatus and method which carries out effective sterilization, quickly, with no toxic residues and with emissions which present no environmental safety hazard.

It is another object of this invention to provide an economical sterilizing system which is safe and effective for use in a hospital environment.

It is a still further object of this invention to provide effective sterilization at a temperature not exceeding 140° C., with an effective kill rate, and with non-explosive gas mixtures containing hydrogen.

The method of this invention for plasma sterilization comprises exposing an article to be sterilized to a plasma generated from a gaseous mixture of argon, helium, nitrogen or mixtures thereof, mixed with oxygen and/or hydrogen at temperatures of less than 63° C., a pressure of from 0.1 to 10 torr, and a treatment time of at least 5 and preferably from 10 to 15 minutes. For sterilizing packaged goods, the gas mixtures from which the plasma is generated can contain from 1 to 21 (v/v) % oxygen and from 1 to 20 (v/v) % hydrogen, the balance being argon, helium, nitrogen, or mixtures thereof, and optional small quantities of other inert gases. The gas mixtures producing plasmas for sterilizing packages preferably contain from 1 to 10 (v/v) % oxygen and from 2 to 8 (v/v) % hydrogen, and optimally contain from 2 to 8 (v/v) % oxygen and from 3 to 7 (v/v) % hydrogen. In an alternate embodiment, packaged goods are sterilized by treatment for at least 15 minutes and preferably at least 1 to 5 hours with plasma generated from a gas mixture containing from 1 to 10 (v/v) % hydrogen and from 90 to 99 (v/v) % argon, helium, nitrogen or mixtures thereof, with little or no amounts of oxygen being present. The optimum mixture comprises 5 (v/v) % hydrogen and about 95 (v/v) % argon.

Contaminated goods may require a protein removal or deproteinizing step prior to the sterilization step. Plasma deproteinizing can be effected by treating the objects to be sterilized at temperatures of less than 63° C. and pressures of from 1 to 10 torr with plasma generated from a gas mixture of from 90 to 100 (v/v) % oxygen, from 0 to 10 (v/v) % argon and optional amounts of hydrogen. Deproteinizing is effected by treating the contaminated articles with plasmas generated from these gas mixtures for at least 1 minute and preferably at least 5 minutes.

Objects which are resistant to oxidation such as metallic surgical instruments can be sterilized by treatment for at least 1 minute and preferably for at least 10 minutes with plasma. The plasma is generated from a gas mixture containing from 10 to 40 (v/v) % oxygen; from 60 to 90 (v/v) % argon, helium, nitrogen, or mixtures thereof; and optional amounts of hydrogen and/or inert gases. The plasma sterilization is carried out at a temperature of 63° C. or less and a pressure of from 1 to 10 torr. The plasma can be generated from air (21 v/v % oxygen and 78 v/v % nitrogen, etc.), for example.

The gas plasma is preferably generated in an applied electromagnetic field in a plasma generating chamber at a pressure of from 0.3 to 10 torr and preferably from 1 to 5 torr, and the gas plasma produced therein is introduced into a separate sterilization chamber where the article to be sterilized is exposed to the gas plasma.

The apparatus of this invention for plasma sterilization of articles comprises a plasma generator and a sterilizing chamber, the plasma generator having an inlet for receiving a gas mixture. A plasma generating chamber for generating plasma from a mixture of gases communicates with the inlet, and with an outlet for communicating with the sterilizing chamber. The plasma generating chamber comprises a generator tube positioned in an electromagnetic field zone of an electromagnetic wave generator, the outlet thereof preferably having a restriction means for maintaining the gas pressure in the plasma generating chamber at from 2 to 6 torr.

The generator tube is a quartz tube positioned in an electromagnetic field zone of a waveguide, the electromagnetic field being driven or generated by a magnetron, klystron or RF coil, for example. When the electromagnetic wave generator is a magnetron, the magnetron can be positioned in a waveguide defining an electromagnetic field zone, and the generator tube passes through the waveguide. When it comprises a plurality of magnetrons, each magnetron is positioned in a separate waveguide defining a respective electromagnetic field zone, and a generator tube passes through each waveguide. It can alternatively comprise a single magnetron, and a plurality of generator tubes can pass through the waveguide, each generator tube being positioned to absorb a portion of electromagnetic field energy from the electromagnetic field. In that event, the waveguide has a sidewall and a central axis, the magnetron is positioned at one end of the waveguide, and each of the generator tubes is positioned in at a different distance from the magnetron and sidewall. Preferably, the apparatus comprises a gas distributor communicating with the plasma generator chamber means and with the sterilizing chamber and positioned to change the flow direction of the plasma through an angle of at least 90° before discharging it into the sterilizing chamber, whereby the hot nascent plasma does not directly impinge on the articles being sterilized.

DETAILED DESCRIPTION OF THE INVENTION

Hospitals originally relied on disinfectants and steam autoclaves for sterilizing implements. In more recent years, ethylene oxide gas sterilization has made possible the sterilization of packaged articles, drugs and medical supplies, and hospital systems are highly dependent upon these procedures. Ethylene oxide is now known to be a dangerous carcinogen, however, and a number of new state laws protecting worker safety and the environment are precluding further use of ethylene oxide sterilizers in hospital environments.

Numerous gas plasma sterilizers using a wide variety of gases have been described in the patent literature. A few have been commercially produced. A few have focused on residue contamination problems. The previously described gas sterilizers either fail to satisfy current regulatory residue and exhaust emission safety standards of several states, because they either leave unacceptable residues, produce exhaust emissions which are potentially hazardous to hospital personal, or cause unacceptable destruction of packaging materials. Substituting one hazard for another, they are thus not satisfactory for replacing ethylene oxide sterilizers.

The gas sterilizer of this invention produces a plasma from gas mixtures containing argon, helium and/or nitrogen; and oxygen and/or hydrogen, optionally containing inert gases and carbon dioxide. The exhaust gas products fully satisfy current environmental and worker safety concerns, the products of the plasma being almost entirely water vapor, carbon dioxide and non-toxic gases normally found in the atmosphere.

The term "plasma" as used herein is defined to include any portion of the gas or vapors which contain electrons, ions, free radicals, dissociated and/or excited atoms or molecules produced as a result of the applied electric or electromagnetic field including any accompanying radiation which might be produced. The electromagnetic field can cover a broad frequency range, and can be produced by a magnetron, klystron or RF coil. For purposes of clarity of presentation and not by way of limitation, the description hereinafter describes the use of a magnetron as the electromagnetic field source, and the use of all other suitable sources of the electromagnetic field required for plasma production are intended to be included in this invention, including without limitation, magnetrons, klystron tubes, RF coils, and the like.

The term "sterilization" connotes a process by which all viable forms of microorganisms are destroyed or removed from an object. Since microorganisms die according to first order chemical kinetics, it is customary to define sterility in terms of "probability of survivors". The practical goal of a sterilization process is therefore measured as a probability (e.g., $10^{-3}$, $10^{-6}$, $10^{-12}$), the probability indicating the lethal effect of a particular sterilizing dose or regimen. It is usual to assume increased time of exposure to a set of sterilizing conditions will decrease the probability of survivors accordingly. Doubling the sterilizing time of identical conditions would result in a doubling of the exponent of the probability term, for example $10^{-6}$ would become $10^{-12}$.

Figure 1:
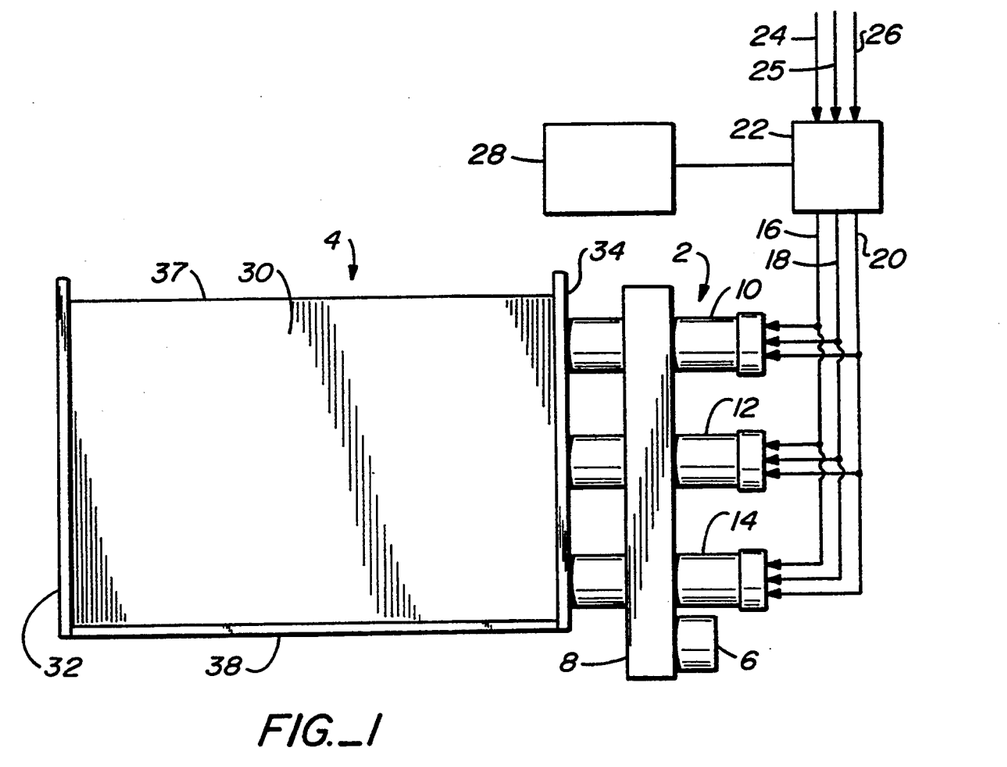
FIG. 1 is a top view of a plasma sterilizer of this invention.
Figure 2:
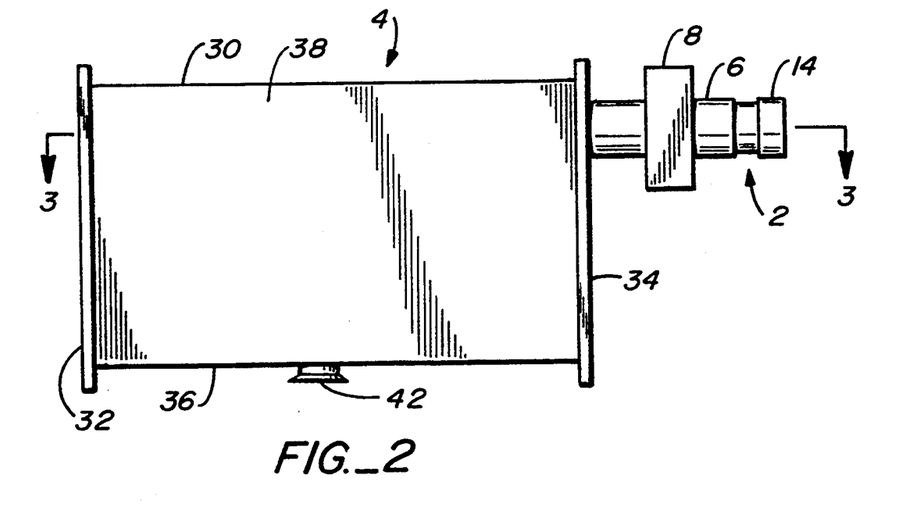
FIG. 2 is a front view of the plasma sterilizer embodiment of FIG. 1.

FIG. 1 is a top view and FIG. 2 is a front view of a single waveguide plasma sterilizer embodiment of this invention. The plasma sterilizer has a plasma generator 2 and a sterilizing chamber 4. The plasma generator 2 comprises an electromagnetic field generator such as a magnetron 6 and a waveguide 8 which directs the electromagnetic field. The plasma source gases are directed into plasma generating and delivering tubes 10, 12, and 14 by feeder tubes from gas delivery tubes 16, 18 and 20 leading from the control valve complex 22. Individual gases are fed from the pressured gas sources (not shown) by inlet lines 24, 25 and 26. The operation of the control valves in valve complex 22 is controlled by the central processing unit (CPU) 28 by standard procedures. The control valves and CPU can be any of the conventional, standard devices used for gas flow control in plasma generating equipment.

The sterilizing chamber 4 comprises top plate 30, side plates 32 and 34, bottom plate 36, back plate 37 and front sealing door 38 through which articles or materials to be sterilized are placed in the chamber. The plates are attached together in a sealed relationship to form a vacuum chamber, such as by welding. The door 38 is secured in a sealed relationship with the sterilizing chamber. It is hinged at the top, side or bottom with conventional hinge pins (structure not shown) to swing against abutting surfaces and an O-ring seal 40 (FIG. 3) of the side, top and bottom plates, where the pressure difference between the internal chamber vacuum pressure and the surrounding atmospheric pressure holds it tightly in place.

The plates and door can be made of any material having the strength required to withstand the external atmospheric pressure when the chamber is evacuated. Stainless steel or aluminum plates and door are preferred. The internal surface material of the chamber is critical and greatly affects the number of killing species available in the chamber. An optimum material is pure (98%) aluminum which can be applied either as a liner or as a flame-sprayed coating on all internal walls of the stainless steel chamber. An alternate material is nickel.

The gases are exhausted from the sterilizing chamber through exhaust outlet port 42 to a conventional vacuum pump system (not shown).

Figure 3:
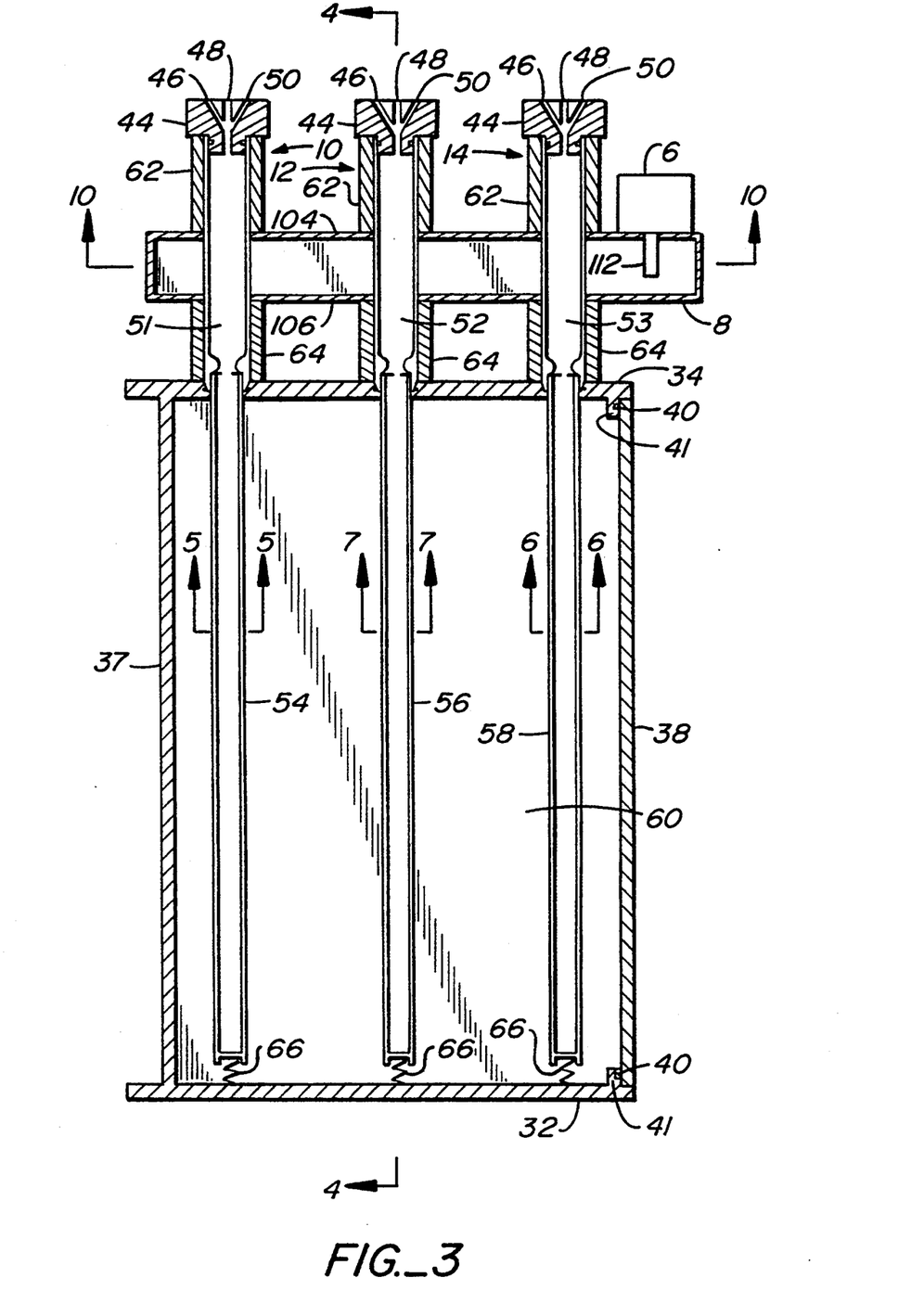
FIG. 3 is a cross-sectional view of the plasma sterilizer embodiment of FIG. 1 and FIG. 2, taken along the line 3—3 in FIG. 2.
Figure 4:
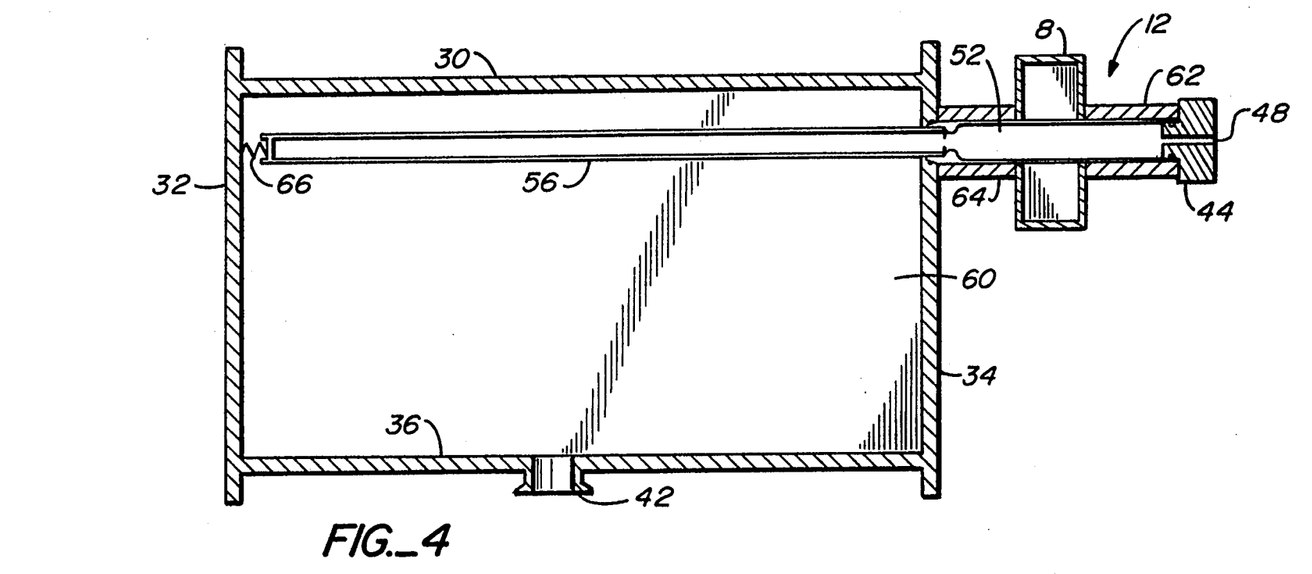
FIG. 4 is a cross-sectional view of the plasma sterilizer embodiment of FIG. 3, taken along the line 4—4.

FIG. 3 is a top cross-sectional view of the plasma sterilizer embodiment of FIG. 1 and FIG. 2, taken along the line 3—3 in FIG. 2. FIG. 4 is a side cross-sectional view of the plasma sterilizer embodiment of FIG. 1 and FIG. 3, taken along the line 4—4 in FIG. 3. Each of the plasma generators 10, 12 and 14 comprise an inlet cap 44 with gas inlet ports 46, 48 and 50 leading to a respective gas generator tube 51, 52 or 53 leading through the waveguide 8. In the waveguide 8, the gases are energized and convert in tubes 51, 52 and 53 to a plasma. The gas generator tube directs the plasma flow into the gas distribution tubes 54, 56 and 58 from which the plasma is fed into the sterilizing chamber 60. The gas generator tubes are enclosed in tubular metal cooling tubes 62 and 64. The caps 44 and the cooling tubes 62 and 64 are preferably provided with groves or cooling fins (not shown) in a conventional manner to increase their efficiency in removing heat from gas generator tubes. The distal ends of the gas distribution tubes 54, 56 and 58 are supported by spring-biased end supports 66 mounted on sideplate 32.

The door 38 is held in sealing engagement by atmospheric pressure against the O-ring seal 40 mounted in the flange 41 extending from the side plates 32 and 34, and the top and bottom plates 30 and 36 (not shown). Optionally, additional conventional closure clamp or latch devices can be used to insure closure of the door before chamber evacuation is initiated.

Figure 5:
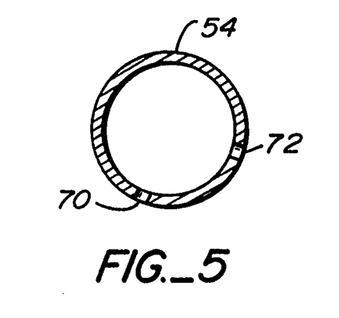
FIG. 5 is a cross-sectional view of tube 54 taken along line 5—5 in FIG. 3.
Figure 6:
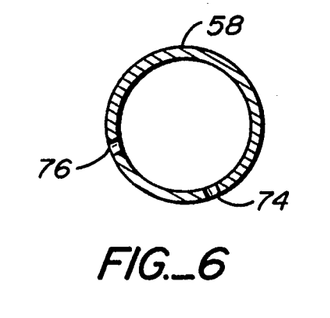
FIG. 6 is a cross-sectional view of tube 58 taken along line 6—6 in FIG. 3.
Figure 7:
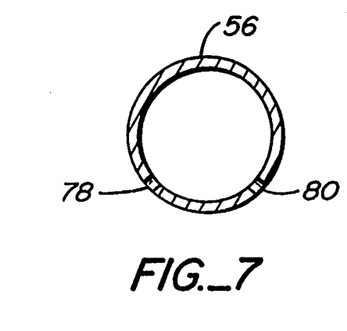
FIG. 7 is a cross-sectional view of tube 56 taken along line 7—7 in FIG. 3.

FIGS. 5, 6 and 7 are cross-sectional views of gas distribution tubes 54, 58 and 56, respectively, showing angular positions of the gas distribution outlet ports. The outlet ports are positioned to provide plasma flow to all lower portions of the sterilizing chamber 60 where articles to be sterilized are placed. Tube 54 shown in FIG. 5 is placed adjacent back plate 37 and directs plasma gases downward and toward the lower center of the chamber through outlet ports 70 and 72, respectively. Tube 58 shown in FIG. 6 is placed adjacent the door 38 and directs plasma gases downward and toward the lower center of the chamber through outlet ports 74 and 76, respectively. Tube 56 shown in FIG. 7 is placed in the central portion of the chamber 60 and directs plasma gases laterally downward through outlet ports 78 and 80. The outlet ports shown for the distribution tubes are representative and can be changed to any other configuration which achieves optimal plasma distribution to the sterilizing zone or zones of the chamber. Although only one angular arrangement is shown, each tube can have more than one angular set of outlet ports, each having different angles, along the length of the tube, as desired. The choice of outlet port angles and locations should be selected in view of how the articles to be sterilized are to be placed in the chamber and the type of article to be sterilized.

The plasma is directed through a change of direction, preferably at least 90°, before discharging it into the sterilizing chamber. This prevents direct impingement of hot plasma onto the articles being sterilized, greatly reducing the oxidation of sensitive packaging materials by the activated oxygen atoms in the plasma.

Figure 8:
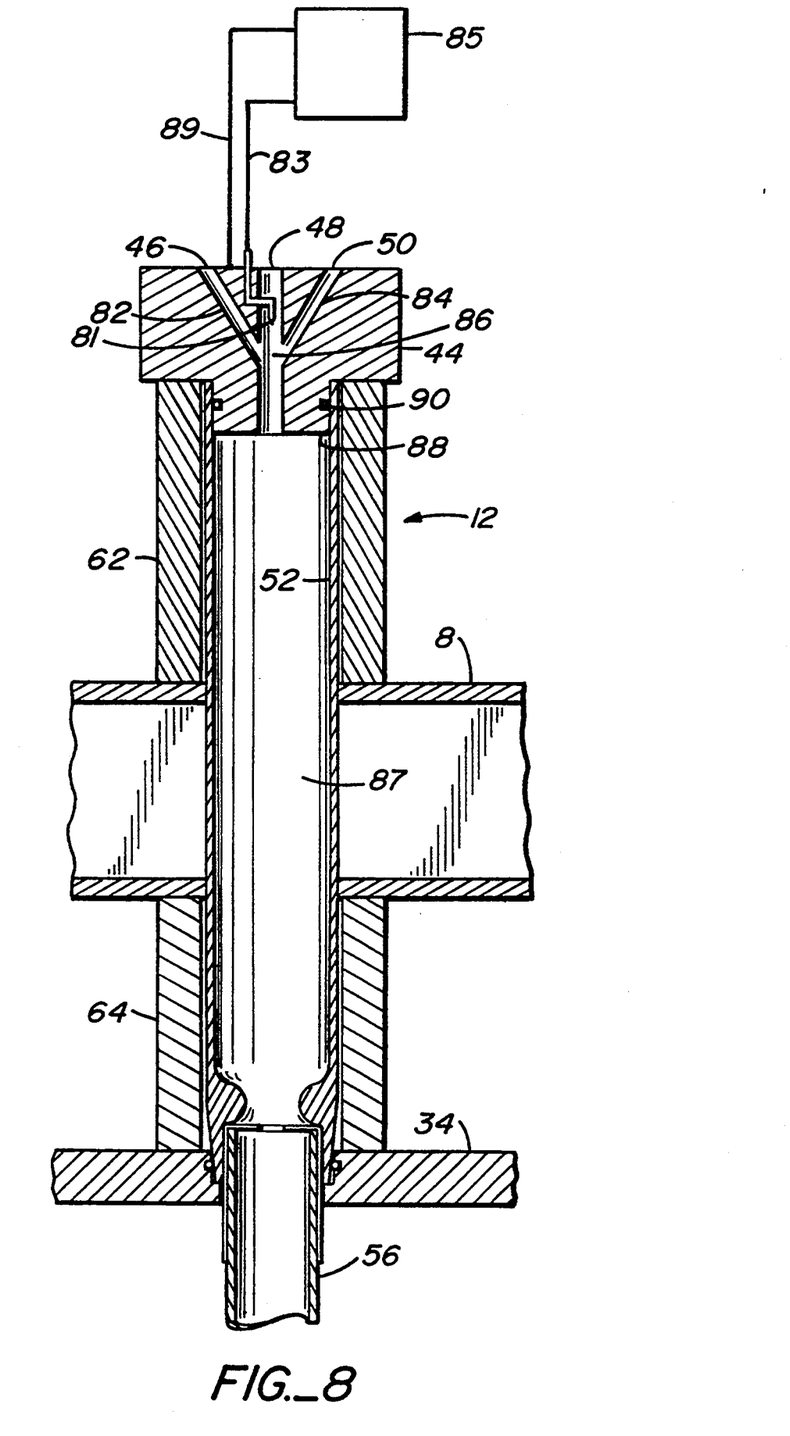
FIG. 8 is a partial cross-sectional view of the plasma generator tube and assembly of the embodiment of FIG. 1.
Figure 9:
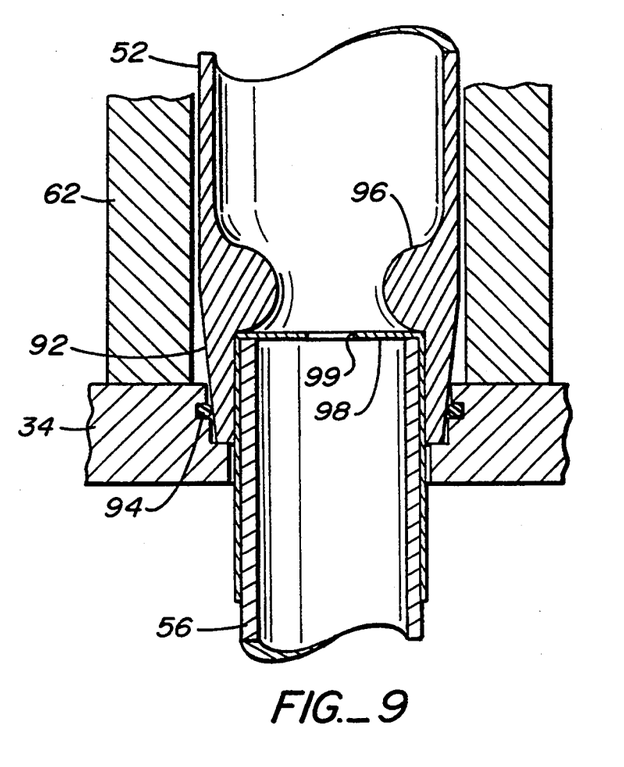
FIG. 9 is a partial, fragmentary, cross-sectional detail view of the plasma generator tube of the plasma generator shown in FIG. 8.

FIG. 8 is a partial top cross-sectional detail fragmentary view of plasma generator 12 of FIG. 3, and FIG. 9 is a more detailed view of the plasma generator tube outlet assembly shown in FIG. 3. The gas inlet ports 46 and 50 in the gas inlet cap 44 are connected by passageways 82 and 84 to the gas inlet passageway 86 leading from inlet port 48. The gases fed to the inlet ports are mixed in the passageway 86. The gas mixture passes into the proximal end of the tube 52 and through the excitation zone 87 within the waveguide 8 where the plasma is formed. The proximal end of the plasma generator tube 52 is supported on cylindrical projection 88. O-ring 90 or another type of seal forms a gas-tight seal therewith, thereby maintaining a reduced pressure in the tube 52 and preventing leakage of atmospheric gas into the system.

In this sectional view, an optional plasma starter ionizer is shown. The tip 81 is connected by an insulated conduit 83 (shown schematically) to a power supply 85 which can be powered with a standard 115 V AC power source. A ground conduit 89 from the power supply connects to the gas inlet cap 44. The electric field ionizes a portion of the gas molecules flowing from opening 48 through passageway 86, the ionized gases quickly supporting a plasma as the gases pass through the zone 87. The ionizer can be placed in any of the inlet gas passageways of any of the embodiments of this invention.

Referring to FIG. 9, the outer surface 92 of the distal end of the plasma generator tube 52 is tapered inward and is sealed by O-ring 94 or other form of seal with the backplate 37. The distal end of tube 52 has increased thickness and forms a smooth surfaced venturi restriction 96 of reduced cross-sectional area. Cap 98 positioned on the proximal end of plasma distribution tube 56 has a preselected restrictive opening 99 of further reduced cross-sectional area. These restrictions, are critical aspects of the preferred embodiment of this invention, creating a pressure difference between the low pressure plasma generating zone 87 and the vacuum pressure in the distribution tube 56 and sterilizing chamber 60.

The diameter of the restriction opening 99 is selected to maintain a back pressure of from 0.3 to 10 torr, preferably from 1 to 5 torr and optimally from 5 to 6 torr in the plasma generating zone with a vacuum chamber pressure in the range of from 0.3 to 2 torr. This pressure provides optimum energy consumption and plasma generation with gas mixtures containing oxygen; argon, helium and/or nitrogen; and/or hydrogen and is a major factor for the production of a high yield of plasma at a minimum temperature and with the minimum power requirement achieved with the device of this invention. For most operating parameters, the restriction 99 can have a diameter of from 4.82 to 8.00 mm and preferably from 6.28 to 6.54 mm.

Figure 10:
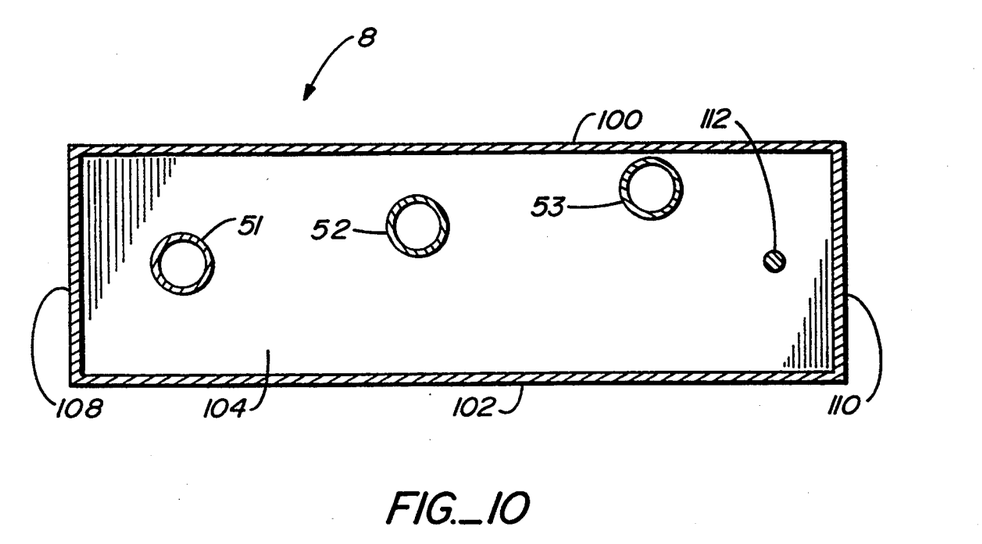
FIG. 10 is a cross-sectional view of the waveguide of the embodiment of FIG. 1, taken along the line 10—10 in FIG. 3.

FIG. 10 is a cross-sectional view of the waveguide of the embodiment of FIG. 1, taken along the line 10—10 in FIG. 3. The waveguide is formed of top and bottom plates 100 and 102, side plates 104 and 106 (FIG. 3), and end plates 108 and 110, welded or bolted together. A single magnetron rod 112 is placed in the end of the waveguide 8. The plasma generating tubes 51, 52 and 53 are positioned in the waveguide 8. The positions of the plasma generating tubes are selected to provide maximum conversion of the electromagnetic field energy to plasma. Tube 53 is positioned in a zone to interact with a third of the field and not with zones of the field which will interact with tubes 51 and 52. Tube 52 is positioned in a zone to interact with a third of the field (half of the remaining field) and not with the field zone which will interact with tube 51. Tube 51 is positioned to interact maximally with the remainder of the field. With this configuration, a single magnetron can be used to generate plasma with a plurality of gas generating tubes. The precise placement of the tubes which will accomplish this result will depend upon the dimensions of the wave guide and the wavelength or frequency of the energizing wave.

Three tubes have been shown in FIG. 10 by way of example and not by way of limitation. Any number, odd or even, of tubes can be used up until the total power of the electromagnetic field is absorbed.

Figure 11:
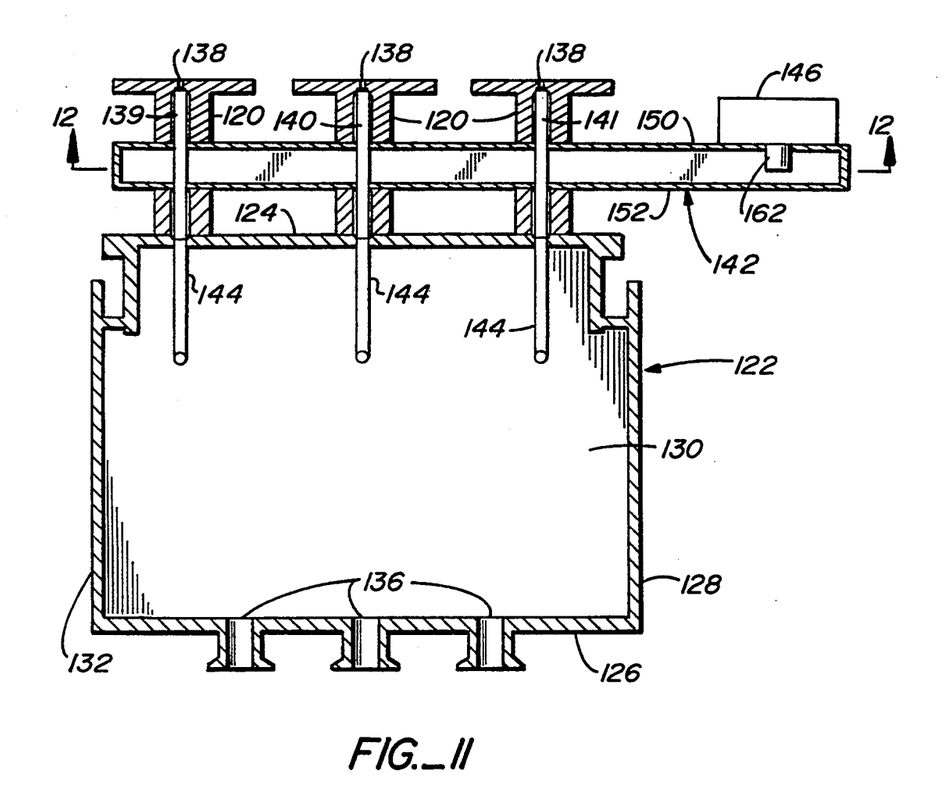
FIG. 11 is a side cross-sectional view of an alternate single waveguide embodiment of the plasma sterilizer of this invention.

FIG. 11 is a front cross-sectional view of an alternate single wave guide embodiment of the plasma sterilizer of this invention. Three plasma generating units 120 are positioned above the sterilizing chamber 122 defined by upper plate 124, lower plate 126, back plate 130, back plate 130 and side plates 128 and 132. The door plate (not shown) can be mounted to the front of the chamber as described above with respect to FIG. 2 and FIG. 3 and forms a sealed engagement with the front edges of the chamber walls. The gases are exhausted from the chamber through exhaust ports 136 in the floor plate 126.

The plasma generators comprise an inlet port for mixed gases 138 leading to the plasma generating tubes 139, 140 and 141 positioned in the waveguide 142 where the gases are energized and converted to a plasma. The plasma is directed by the plasma distributors 144 to the interior of the sterilizing chamber 122. Each plasma distributor 144 can have a T-configuration described below in detail with respect to the embodiment of FIG. 14. The distributor can have any shape and size which distributes the plasma gases uniformly thoroughout the sterilizing chamber. The plasma generating source in this embodiment is a magnetron 146 positioned at the end of the waveguide 142.

Figure 12:
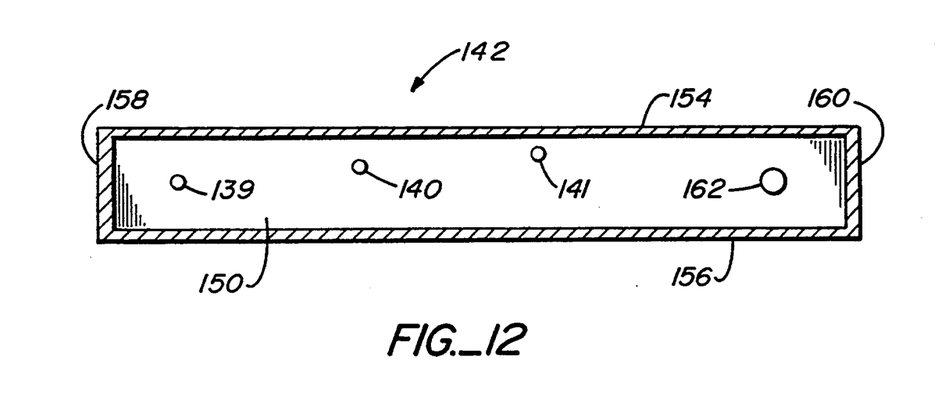
FIG. 12 is a cross-sectional view of the waveguide of the embodiment of FIG. 11, taken along the line 12—12.

FIG. 12 is a cross-sectional view of the waveguide of embodiment of FIG. 11, taken along line 12—12 in FIG. 11. The waveguide is formed of top and bottom plates 150 and 152 (FIG. 11), side plates 154 and 156, and end plates 158 and 160, welded or bolted together. A single magnetron rod 162 is placed in the end of the waveguide 142. The plasma generating tubes 139, 140 and 141 are positioned in the waveguide 142. The positions of the plasma generating tubes are selected to provide maximum conversion of the electromagnetic field energy to plasma. Tube 141 is positioned in a zone to interact with a third of the field and net with zones of the field which will interact with tubes 140 and 139. Tube 140 is positioned in a zone to interact with a third of the field (half of the remaining field) and not with the field zone which will interact with tube 139. Tube 139 is positioned to interact maximally with the remainder of the field. With this configuration, a single magnetron can be used to generate plasma with a plurality of gas generating tubes. The precise placement of the tubes which will accomplish this result will depend upon the dimensions of the wave guide and the wavelength or frequency of the energizing wave. Three tubes have been shown in FIG. 12 by way of example and not by way of limitation. Any number, odd or even, of tubes can be used up until the total power of the electromagnetic field is absorbed.

The detailed construction of the plasma generator tube and plasma distribution tube seals and flow restrictors have the same configuration as the corresponding elements in the embodiment of FIG. 11 and are described in greater detail hereinabove in conjunction therewith.

Figure 13:
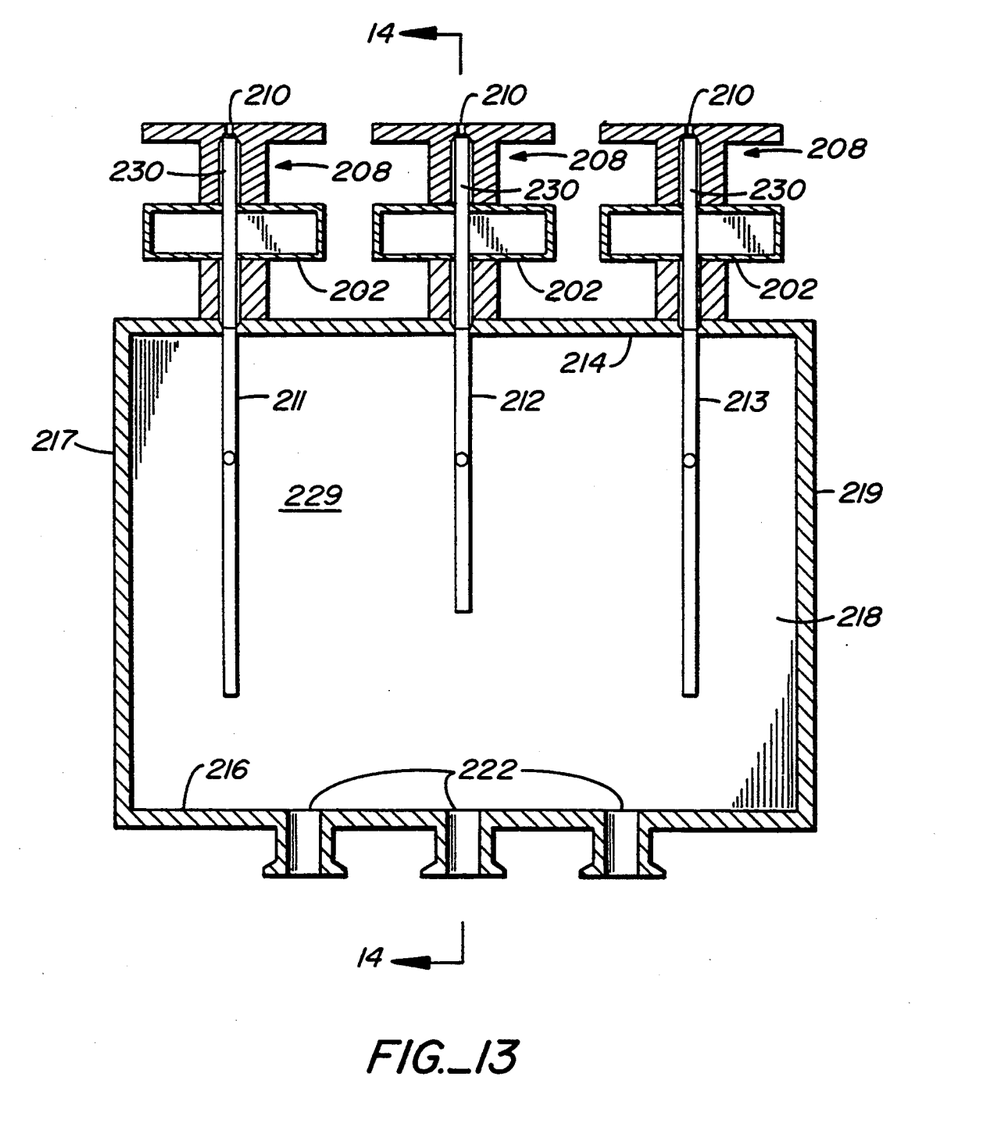
FIG. 13 is a side cross-sectional view of a multiple magnetron embodiment of this invention.
Figure 14:
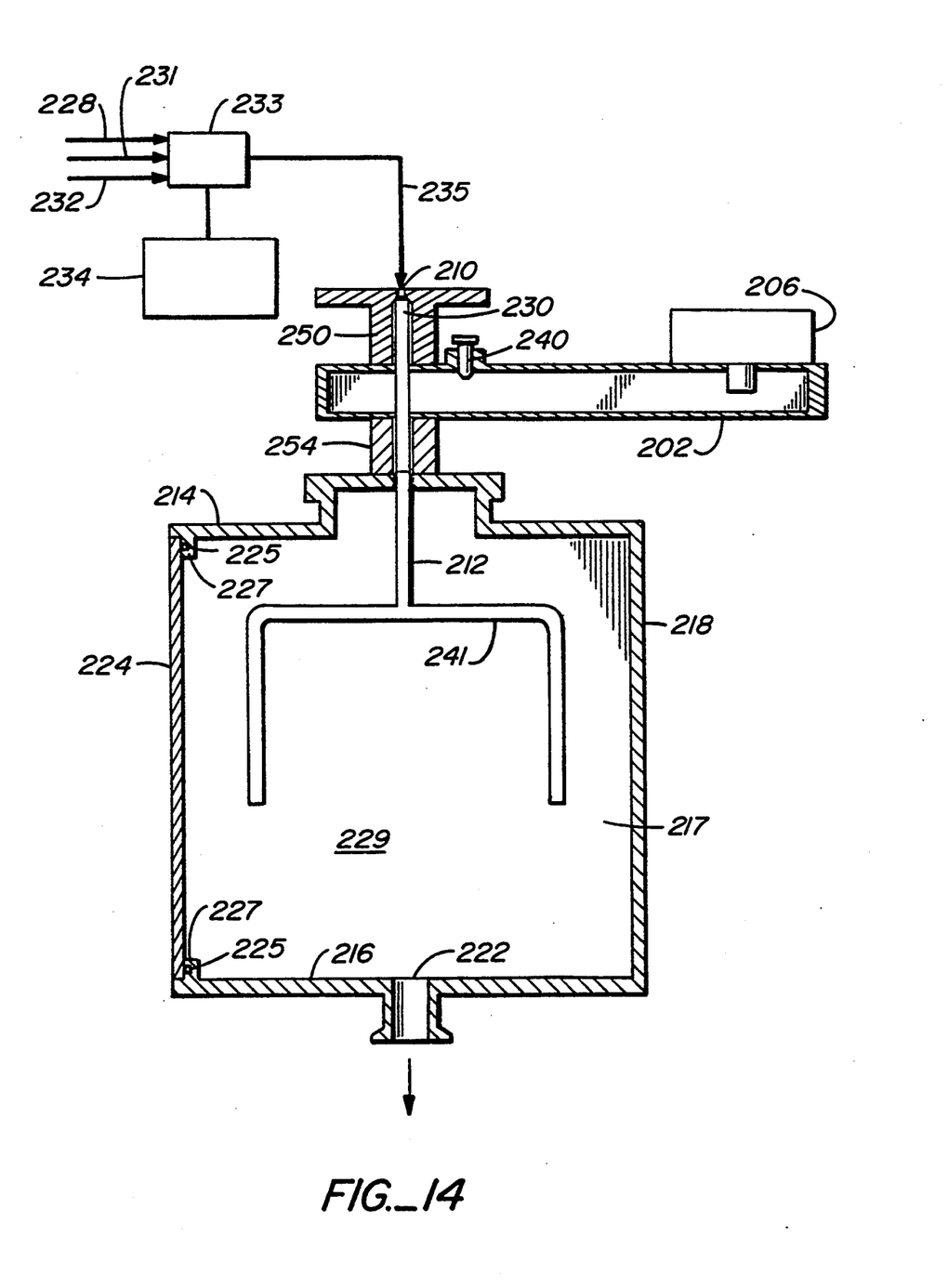
FIG. 14 is a front cross-sectional view of the multiple waveguide embodiment of the plasma sterilizer of this invention, taken along the line 14—14 of FIG. 13.

FIG. 13 is a front cross-sectional view of a multiple magnetron embodiment of this invention, and FIG. 14 is a side cross-sectional view taken along the line 14—14 in FIG. 13. Three plasma generators 208 of this embodiment are positioned above the sterilizing chamber cavity 229, each producing a plasma generated from a gas mixture of oxygen; argon, helium and/or nitrogen; and/or hydrogen introduced through inlets 210 to a plasma generating tube 230 positioned in the respective waveguides 202. The plasma produced is fed by plasma generating tubes 230 through respective gas distributors 211, 212 and 213 into the sterilizing chamber 229. The distributor tubes can have any length and configuration required for distributing the plasma gases uniformly thoroughout the sterilizing chamber. Distribution tubes made of non-fragile materials are particularly advantageous. Suitable non-fragile tubes can be made of oxidation resistant metals such as stainless steel. Optimally, they are made of a plasma resistant polymer such as a fluorocarbon polymer, e.g., TEFLON.

The sterilizing chamber 229 is constructed from metal plates welded to form a gas-tight construction which is able to withstand external pressures when the chamber is evacuated. The construction comprises top plate 214, bottom plate 216, back plate 218, side plates 217 and 219. Exhaust ports 222 are mounted in the bottom plate 216. The door 224 is supported by conventional pin hinges or the like (not shown) mounted on the side, top or bottom of the chamber walls as described above with respect to the embodiment of FIG. 1. The door 224 is held in sealing engagement by atmospheric pressure against the O-ring seal 225 mounted in the flange 227 extending from the side plates 217 and 219, and the top and bottom plates 214 and 216. Optionally, additional conventional closure clamp or latch devices can be used to insure closure of the door before chamber evacuation is initiated.

Referring to FIG. 14, the oxygen; argon, helium and/or nitrogen; and/or hydrogen gases are fed by inlet lines 228, 231 and 232 to the control valve and gas mixing unit 233 controlled by CPU 234. The gas mixture is fed to the inlet port 210 by conduit 235 and then to the plasma generating tube 230 where it is energized to form a gas plasma. The control valves and CPU can be any of the conventional, standard devices used for gas flow control in plasma generating equipment. The waveguide 202 guides the electromagnetic waves generated by the magnetron 206 in a pattern which concentrates the electromagnetic energy in a zone in which the plasma generator tube 230 is positioned. A tuning rod 240 can be vertically positioned to tune the electromagnetic waves to provide optimum plasma generation. The gas plasma is then fed to the gas distributor 212 and its Y- or T-distribution section 241. The horizontal distributors have angular outlet ports positioned and with angular displacement as described with respect to the preferred embodiment of FIGS. 5, 6 and 7. The plasma is directed through a change of direction of 90° twice before it is discharged into the sterilizing chamber. This prevents direct impingement of hot nascent plasma onto the articles being sterilized, greatly reducing the oxidation of sensitive packaging materials by the activated oxygen atoms in the plasma.

Figure 15:
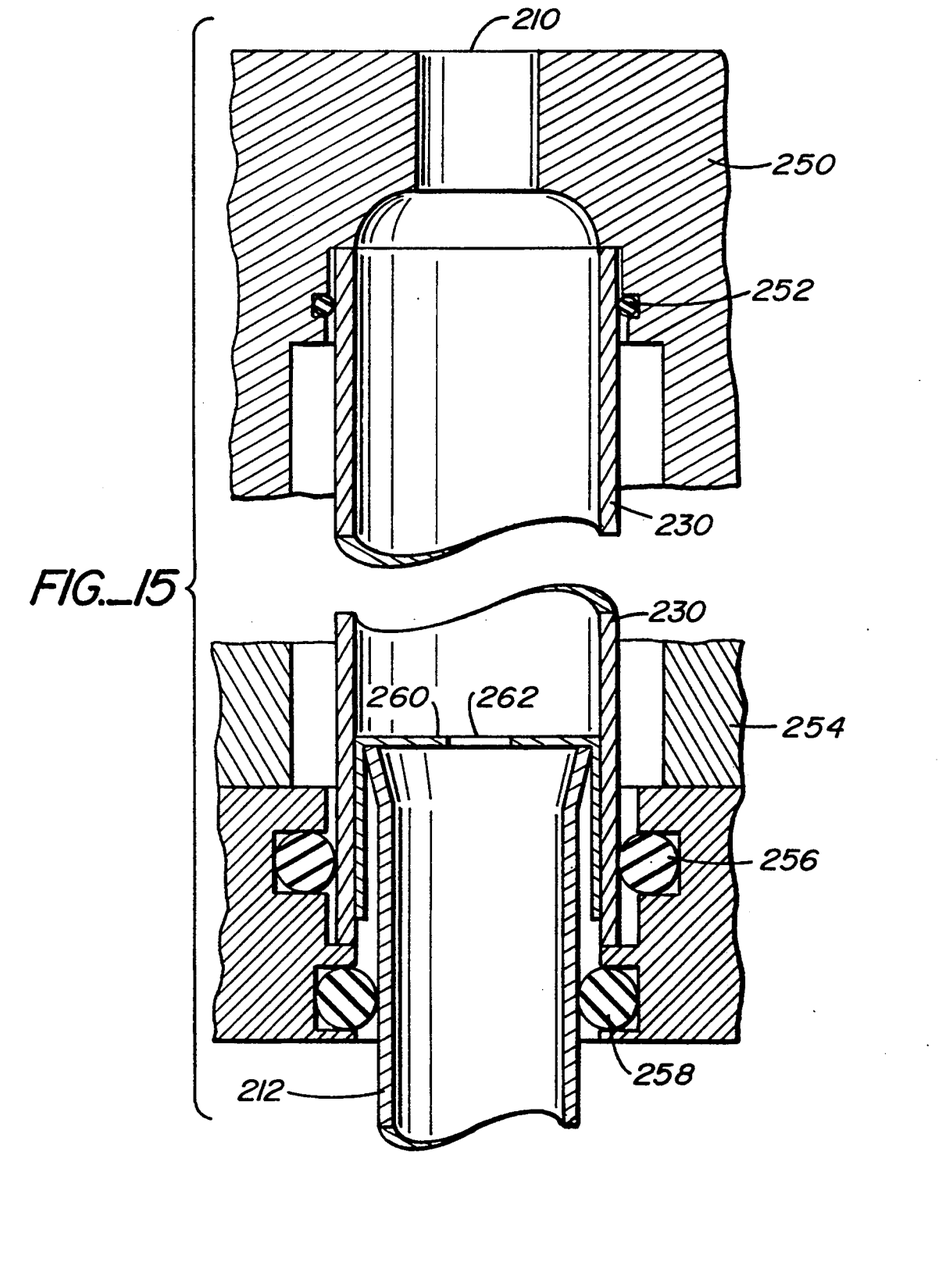
FIG. 15 is a partial cross-sectional view of the plasma generator tube and assembly of the embodiment of FIG. 13.

FIG. 15 is a fragmentary, cross-sectional view of the plasma generating tube of the plasma generator shown in FIG. 14, showing details of the tube construction and its connection with the gas distributor tube. The tube 230 is held in a sealed engagement with the heat radiating cap 250 by O-ring 252 or a similar seal. The lower distal end of the tube is also held in a sealed engagement with the lower heat radiator sleeve 254 by an O-ring 256. The proximal end of the distribution tube 212 extends into the distal end of tube 230 and is held in a sealed relationship with the lower heat radiator sleeve by an O-ring 258. Cap 260 is positioned on the proximal end of plasma distribution tube 212 and has a preselected restrictive opening 262 of further reduced cross-sectional area. As described with respect to the embodiment shown in FIG. 9, the restriction is a critical aspect of the invention, creating a pressure difference between the low pressure plasma generating zone and the vacuum pressure in the distribution tube and sterilizing chamber.

The diameter of the restriction opening 262 is selected to maintain a back pressure of from 0.3 to 10 torr and preferably from 1 to 5 torr in the plasma generating zone with a vacuum chamber pressure in the range of from 0.3 to 2 torr. This pressure provides optimum energy consumption and plasma generation with gas mixtures of oxygen; argon, helium and/or nitrogen; and/or hydrogen and is a major factor for the production of a high yield of plasma at a minimum temperature and with the minimum power requirement achieved with the device of this invention. For most operating parameters, the restriction 262 can have a diameter of from 4.82 to 8.00 mm and preferably from 6.28 to 6.54 mm.

The embodiments of this invention have been presented with three plasma generating units. The number of generating units is not critical, being selected to provide a good plasma distribution in the particular sterilizing chamber used. Any desired number of plasma generators can be used with each sterilizing chamber and are intended to be included within the scope of this invention. It will be also be readily apparent that any number of gas plasma tubes can be positioned to interact with the electromagnetic field generated from a single magnetron with this waveguide configuration, and that other waveguide configurations can be used to achieve this effect. The preferred plasma generating tubes and plasma distributing tubes are made of quartz. However, any other materials with the necessary physical, chemical and electrical properties for plasma generation in an electromagnetic field can be used for the plasma generating tubes. Similary, the conduits and tubing used for transport of plasma from the plasma generator to the sterilizing chamber can be any solid material which has the requisite shape and strength and which is resistant to chemical action and degradation by the plasma gases. Suitable transport conduit materials include quartz and other plasma corrosion resistant glasses; stainless steel and other oxidation resistant metals; oxidation resistant plastics such as fluorocarbon polymers, e.g. TEFLON and the like, and siloxane polymers.

The apparatus of this invention generates a sterilizing plasma from a mixture of oxygen; argon; helium, and/or nitrogen; and hydrogen, or with a mixture of air and hydrogen, supplemented by oxygen or nitrogen to give the desired ratios. The sterilization is carried out at a vacuum pressure of from 0.1 to 10 torr and preferably from 1 to 3 torr. The temperature in the sterilizing chamber is maintained below 63° C. and preferably from 38° to 54° C. Under these conditions, effective sterilization is effected without significant deterioration of packaging materials in which articles to be sterilized may be placed.

The method of this invention for plasma sterilization comprises exposing an article to be sterilized to a plasma generated from a gaseous mixture of argon, helium or nitrogen mixed with oxygen and/or hydrogen at temperatures of less than 63° C., a pressure of from 0.1 to 10 torr, and a treatment time of at least 5, and preferably from 10 to 15 minutes. For sterilizing packaged goods, the gas mixtures from which the plasma is generated can contain from 1 to 21 (v/v) % oxygen and from 1 to 20 (v/v) % hydrogen, the balance being argon, helium and/or nitrogen and optional small quantities of inert gases.

The gas mixtures producing plasmas for sterilizing packages preferably contain from 1 to 10 (v/v) % oxygen and from 2 to 8 (v/v) % hydrogen, and optimally contain from 2 to 8 (v/v) % oxygen and from 3 to 7 (v/v) % hydrogen. Packages are treated for at least 15 minutes and preferably from 1 to 5 hours.

In an alternate embodiment, packaged goods are sterilized by treatment for at least 15 minutes and preferably from 1 to 5 hours with plasma generated from a gas mixture containing from 1 to 10 (v/v) % hydrogen and from 90 to 99 (v/v) % argon, helium and/or nitrogen, with little or no amounts of oxygen being present, the optimum mixture comprising 5 (v/v) % hydrogen and about 95 (v/v) argon.

Contaminated goods may require a deproteinizing step prior to the sterilization step. Plasma deproteinizing can be effected by treating the objects to be sterilized at temperatures of less than 63° C. and pressures of from 1 to 10 torr with plasma generated from a gas mixture of from 90 to 100 (v/v) % oxygen, from 0 to 10 (v/v) % argon and optional amounts of hydrogen. Deproteinizing is effected by treating the contaminated articles with plasmas generated from these gas mixtures for at least 1 minute and preferably for from 1 to 5 minutes. Because of the harshness of the plasma produced by this plasma composition, exposure of packaged goods should be limited to the time effective to remove the original contaminating substances.

Objects which are resistant to oxidation such as metallic surgical instruments can be sterilized by treatment for at least 1 minute and preferably for at least 5 minutes with plasma generated from a gas mixture containing from 10 to 40 (v/v) % oxygen; from 60 to 90 (v/v) % argon, helium and/or nitrogen; and optional amounts of hydrogen and/or inert gases at a temperature of preferably less than 63° C. and a pressure of from 1 to 10 torr. The plasma can be generated from air (21 v/v % oxygen, 78 v/v % nitrogen, etc.), for example.

A residence time of from 5 to 10 minutes is usually sufficient to sterilize most articles. Clean articles packaged in envelopes or other shapes having porous surfaces allowing easy penetration of the plasma are usually completely sterilized within 60 minutes.

In an optimum method of sterilizing, the articles to be sterilized are placed in the sterilizing chamber, supported by conventional grids which permit the plasma to reach all surfaces of the articles. The chamber is closed, the sterilizing chamber is evacuated, plasma generation is begun, and the plasma is directed into and through the sterilizing chamber.

The plasma components have a short life, and quickly decay to form water vapor (gas), carbon dioxide, and other non-toxic components usually found in air. These are fully acceptable as residues or as exhaust gas components.

We claim:

1. A method for plasma sterilization comprising generating a plasma in a plasma generating chamber, passing said plasma from said plasma generating chamber via a restriction means and a plasma distribution means to a sterilizing chamber, effecting sterilization in said sterilizing chamber by exposing to the plasma in said sterilizing chamber for a time period sufficient to effect sterilization, wherein
    said restriction means and said plasma distribution means provide an indirect passageway which prevents direct impingement of nascent plasma generated in said plasma generating chamber into said sterilizing chamber.

2. The method of claim 1 wherein the plasma is generated from a gas mixture containing from 1 to 10 (v/v) % oxygen and from 3 to 7 (v/v) % hydrogen.

3. The method of claim 1 wherein an article is contained within said sterilizing chamber and the article is enclosed in a porous container, and the container is surrounded by the plasma during the treatment.

4. A method for plasma sterilization as in claim 1, wherein:
    said plasma is generated from a mixture of gases comprising a first component consisting of oxygen or hydrogen or a mixture there of and a second component consisting of one or more of argon, helium, nitrogen or mixtures thereof.

5. The method of claim 4 wherein the mixture consists of about 5 (v/v) % hydrogen and about 95 (v/v) % argon, helium, nitrogen or a mixture thereof.

6. A method for plasma sterilization as in claim 1, wherein:
    said plasma is generated from a mixture of gases consisting of from 10 to 40 (v/v) % oxygen; and from 60 to 90 (v/v) % argon, helium, nitrogen, or mixtures thereof.

7. The method of claim 6 wherein the mixture of gases is air.

8. A method for plasma sterilization comprising:
    generating a plasma in a plasma generating chamber; and
    flowing said plasma from said plasma generating chamber via a restriction means and a plasma distribution means into another chamber and maintaining the flow for a time period sufficient to effect sterilization therein, wherein
    said restriction means and said plasma distribution means provide an indirect passageway which prevents direct impingement of nascent plasma generated in said plasma generating chamber onto said another chamber.

* * * * *